US011402315B2

(12) United States Patent
Ramsay et al.

(10) Patent No.: US 11,402,315 B2
(45) Date of Patent: Aug. 2, 2022

(54) ESTIMATING RELATIVE PERMEABILITY AND CAPILLARY PRESSURES OF A GEOLOGICAL FORMATION BASED ON MULTIPHASE UPSCALING

(71) Applicant: Landmark Graphics Corporation, Houston, TX (US)

(72) Inventors: Travis St. George Ramsay, Hockley, TX (US); Aravind Prabhakar, Houston, TX (US)

(73) Assignee: Landmark Graphics Corporation, Houston, TX (US)

( * ) Notice: Subject to any disclaimer, the term of this patent is extended or adjusted under 35 U.S.C. 154(b) by 76 days.

(21) Appl. No.: 16/921,331

(22) Filed: Jul. 6, 2020

(65) Prior Publication Data

US 2022/0003651 A1    Jan. 6, 2022

(51) Int. Cl.
*G01N 15/08* (2006.01)
*E21B 49/02* (2006.01)
*G01N 33/24* (2006.01)

(52) U.S. Cl.
CPC ............. *G01N 15/08* (2013.01); *E21B 49/02* (2013.01); *G01N 33/24* (2013.01)

(58) Field of Classification Search
CPC ........ G01N 15/08; G01N 33/24; E21B 49/02; G01V 11/00
See application file for complete search history.

(56) References Cited

U.S. PATENT DOCUMENTS 6,826,520 B1    11/2004  Khan et al.
8,854,430 B2    10/2014  Varslot et al.
(Continued)

FOREIGN PATENT DOCUMENTS

CN    108593514    9/2018
CN    109800521    5/2019
(Continued)

OTHER PUBLICATIONS

Jalal Dakhelpour-Ghoveifel "Capillary-based method for rock typing in transition zone of carbonate reservoirs" (Year: 2018).*
(Continued)

*Primary Examiner* — Catherine T. Rastovski
*Assistant Examiner* — Kaleria Knox
(74) *Attorney, Agent, or Firm* — Kilpatrick Townsend & Stockton LLP (57) ABSTRACT

A system can access geological data describing a plurality of rock types in a physical rock sample drilled from a reservoir. The system can generate synthetic rock samples and execute single phase upscaling to compute absolute permeabilities for the physical rock sample and the synthetic rock samples. The system can execute a first multiphase upscaling based on the single phase upscaling to determine relative permeabilities for the physical rock sample and the synthetic rock samples. The system can compare the relative permeability of the physical rock sample to the relative permeabilities for the synthetic rock samples and select a synthetic rock sample that varies the least from the physical rock sample. The system can perform at least one additional multiphase upscaling on the physical rock sample and the synthetic rock samples to determine a second multiphase upscaling result and to develop a plan for drilling operations.

19 Claims, 7 Drawing Sheets

(56) References Cited

U.S. PATENT DOCUMENTS

| | | | |
|---|---|---|---|
| 2008/0234988 A1* | 9/2008 | Chen | G01V 11/00 703/1 |
| 2009/0259446 A1 | 10/2009 | Zhang et al. | |
| 2016/0328419 A1* | 11/2016 | Safonov | E21B 49/02 |
| 2018/0320493 A1 | 11/2018 | Ramsay et al. | |
| 2019/0003297 A1 | 1/2019 | Brannigan et al. | |
| 2019/0368994 A1* | 12/2019 | Al Readean | G01N 15/08 |

FOREIGN PATENT DOCUMENTS

| | | | |
|---|---|---|---|
| WO | 2013173540 | 11/2013 | |
| WO | WO-2013173540 A1 * | 11/2013 | E21B 47/00 |
| WO | 2017095395 | 6/2017 | |
| WO | 2018151707 | 8/2018 | |
| WO | 2019090316 | 5/2019 | |

OTHER PUBLICATIONS

Computer Modelling Group Ltd., "Simulation Model-Building Application", 2012, 2 pages.
Halliburton, "Core Insight Solution RSWC", 2019, 4 pages.
Halliburton, "Full-Scale Asset Simulation", 2020, 2 pages.
Halliburton, "Nexus Reservoir Simulation Software", 2014, 8 pages.
Ramsay et al., "Steady-State Relative Permeability Upscaling in Multiporosity/Multipermeability Core Assemblages", Society of Petroleum Engineers, 2017, 21 pages.
Ramsay, "Investigation of Upscaled Rock-Fluid Interaction Devised from Discrete and Automated Steady-State Fractional Flow Methods in Stratified Assemblages", SEG International Exposition and 86th Annual Meeting, 2016, 5 pages.
Ramsay, "The Automation of Steady-State Fractional Flow Upscaling in Stratified and Random Rock Type Structures", Society of Petroleum Engineers, 2019, 17 pages.
Rock Flow Dynamics, "Rock Flow Dynamics", Jul. 2018, 71 pages.
Schlumberger, "Eclipse", 2013, 4 pages.
Sendra—Prores, "SCAL Toolbox", 4 pages.
Thermo Scientific, "PerGeos Software", Digital Rock Visualization, Analysis, and Simulation, 2019, 10 pages.
PCT Application No. PCT/US2020/040898, International Search Report and Written Opinion, dated Mar. 18, 2021, 9 pages.
GB2108067.6, "Combined Search and Examination Report", dated Mar. 1, 2022, 8 pages.

* cited by examiner

ESTIMATING RELATIVE PERMEABILITY AND CAPILLARY PRESSURES OF A GEOLOGICAL FORMATION BASED ON MULTIPHASE UPSCALING

TECHNICAL FIELD

The present disclosure relates generally to oilfield operations and, more particularly, although not necessarily exclusively, to estimating flow unit properties of a geological formation based on multiphase upscaling.

BACKGROUND

Hydrocarbon exploration is the search for hydrocarbons, such as oil or gas, within a subterranean formation. Properties such as relative permeability and capillary pressure of the rock types that make up the subterranean formation can influence hydrocarbon flow properties through the subterranean formation. Physical rock samples from the subterranean formation may be used to simulate properties for a reservoir. But the accuracy of simulations using current techniques may be limited. Inaccurate simulations of reservoirs can result in poor resource management.

Further, operators may resort to acquiring core samples to perform physical laboratory or digital rock technology experiments. These experiments may lead to the determination of multiphase rock-fluid interaction properties. However, information regarding flow unit descriptions proximal to the well where the physical samples were derived is often assumed. The remedy for this assumption may involve acquiring more core samples and performing additional experiments on those core samples. This remedy increases costs as additional core samples must be acquired from a formation.

DETAILED DESCRIPTION

Certain aspects and examples of the present disclosure relate to estimating flow unit properties based on multiphase upscaling. Flow unit properties can include relative permeabilities and capillary pressures for various rock types in a reservoir. Substances with multiple fluids, water, oil, or other liquids, often flow through geological formations. Multiphase upscaling refers to upscaling flow data for a core sample to a reservoir scale. By using a system according to some examples, flow unit properties for the reservoir can be estimated for overall asset management of the reservoir. The techniques described in the present disclosure may reduce costs associated with acquiring and analyzing multiple physical core samples. Base geometric configurations can be used to mimic any core samples and machine learning can be leveraged to address intermediate base geometries that are not developed as a part of the synthetic cores.

The presently described techniques can execute relative permeability and capillary pressure upscaling from physical rock samples using physical laboratory or digital rock technology data. Then, multiphase upscaling can be performed on an ensemble of digital synthetic cores with rock types that have disparate volumetric distributions. The volumetric distributions can be assembled in series, parallel, diagonal, random, or any combination of these with respect to the direction of flow in the core samples. The resulting core-based multiphase upscaling can be upscaled to the scale of a reservoir for overall reservoir asset management.

The techniques can automate the upscaling process and use machine learning to expedite the multiple executions of multiphase upscaling and to model systematic changes in multiphase upscaling results determined by multiphase simulations. In this case, machine learning can improve the performance of the overall workflow by determining multiphase upscaling results derived from intermediate rock type configurations of the synthetic cores. Machine learning can enable the system to estimate flow unit properties needed for reservoir simulation and management from the pore to the core scale in areas outside of where physical data is present.

Illustrative examples are given to introduce the reader to the general subject matter discussed herein and are not intended to limit the scope of the disclosed concepts. The following sections describe various additional features and examples with reference to the drawings in which like numerals indicate like elements, and directional descriptions are used to describe the illustrative aspects, but, like the illustrative aspects, should not be used to limit the present disclosure.

Figure 1:
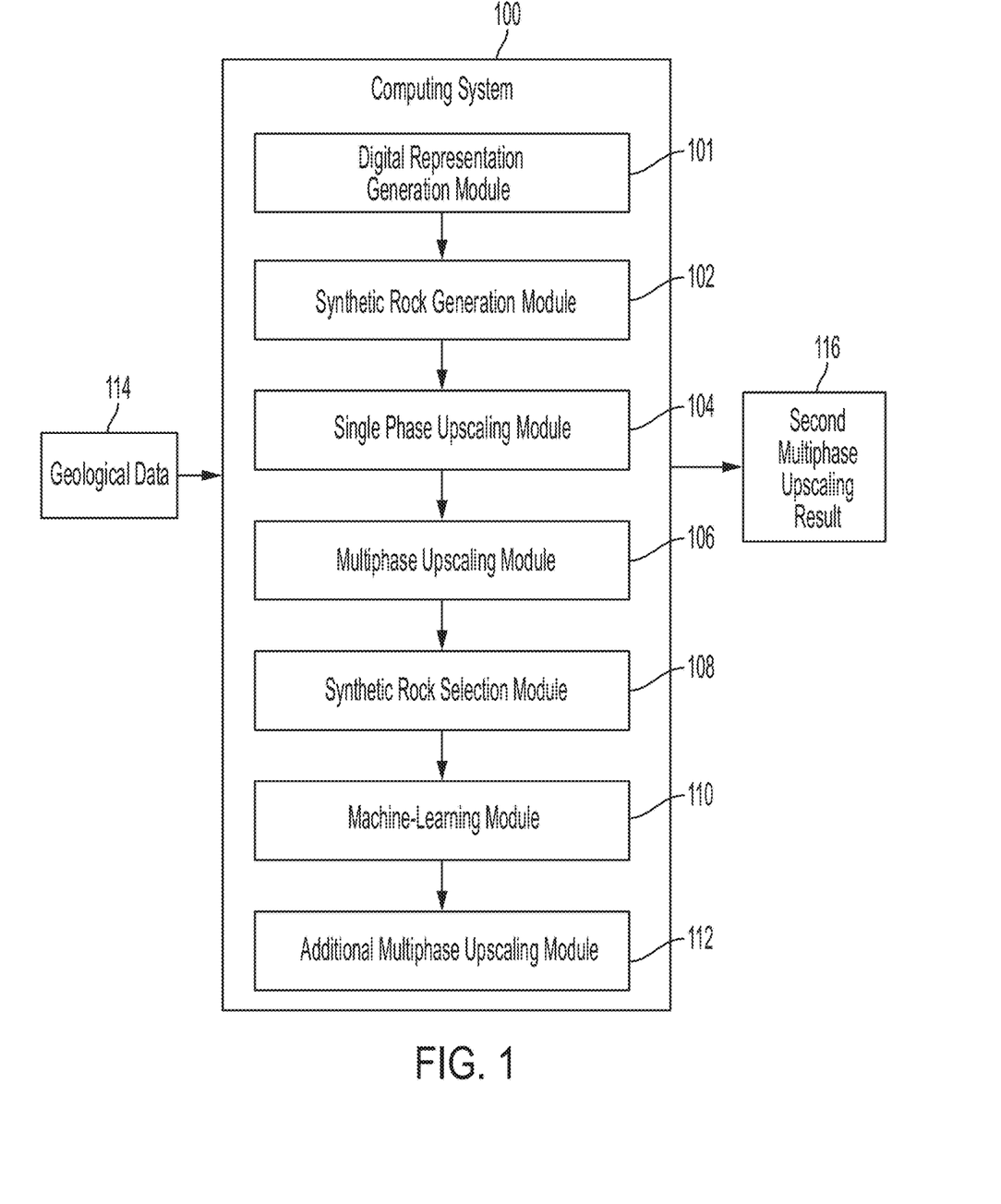
FIG. 1 is a block diagram of a computing system for implementing multiphase upscaling to estimate relative permeability and capillary pressures of a geological formation according to one example of the present disclosure.

FIG. 1 is a block diagram of a computing system 100 for implementing multiphase upscaling to estimate relative permeability and capillary pressures of a geological formation according to one example of the present disclosure. Geological data, such as relative permeability and capillary pressures, can be accessed by the computing system 100. The computing system 100 can include modules for completing operations to estimate relative permeability and capillary pressures of a geological formation. The modules can include a synthetic rock generation module 102, a single phase upscaling module 104, a multiphase upscaling module 106, a synthetic rock selection module 108, a machine-learning module 110, and an additional multiphase upscaling module 112.

In some examples, an operator can obtain a physical rock sample from the geological formation. The physical rock sample can be a plug or core sample composed of multiple rock types. Measurements can be completed on the physical rock sample in a laboratory or using digital rock technology to create geological data 114 for the physical rock sample. The measurements can quantitatively define the rock types in the physical rock sample. For example, the measurements can determine there are two or more types of rock present in the physical rock sample. In some examples, the measurements can indicate the rock types in the physical rock sample and geometric information about the rock types in the physical sample. For example, the measurements can indicate Rock Type A and Rock Type B are present in the physical rock sample. The geometric information can indicate whether the rock types are arranged in parallel, series, diagonally, random, or any combination of these. The measurements can also provide relative permeability and capillary pressures for the rock types in the physical rock sample.

The geological data 114 can include a set of curves corresponding to relative permeability and capillary pressures for the rock types in the physical rock sample. Each rock type in the physical rock sample can be assigned to a curve in the set of curves that corresponds to the relative permeability and capillary pressure of the rock type.

In some examples, the computing system 100 can access the geological data 114 containing the measurements of the physical rock sample. An operator may upload the geological data 114 to the computing system 100. Additionally or alternatively, the geological data 114 can be stored on an additional computing system that the computing system 100 can access.

In some examples, a photograph can be taken of the physical rock sample and the geological data 114 can be generated from the photograph. The computing system 100 can access the geological data 114 and execute the digital representation generation module 101 to generate a digital representation of the physical rock sample from the photograph of the physical rock sample.

In some examples, the computing system 100 can include the synthetic rock generation module 102. The synthetic rock generation module 102 can generate a plurality of synthetic rock samples with disparate volumetric distributions to each other and similar geometric configurations to the physical rock sample. For example, if the physical rock sample is composed of two rock types arranged in parallel, the synthetic rock generation module 102 can generate synthetic rock samples with rock types in parallel. Additionally, one synthetic rock sample can be composed 50% of Rock Type A and 50% of Rock Type B. Another synthetic rock sample can be composed 80% of Rock Type A and 20% of Rock Type B. Other arrangements and percentages of the synthetic rock samples may also be generated by the synthetic rock generation module 102.

In some examples, the computing system 100 can include the single phase upscaling module 104 to compute an absolute permeability for the physical rock sample and absolute permeabilities for the synthetic rock samples. The single phase upscaling module 104 may execute steady-state or unsteady-state upscaling. The absolute permeability can be calculated when a single phase (e.g., water) flows through the rock. The single phase upscaling module 104 can execute operations on the physical rock sample or on a digital representation of the physical rock sample to determine the absolute permeability of the physical rock sample. The single phase upscaling module 104 can execute similar operations on the synthetic rock samples to determine absolute permeabilities of the synthetic rock samples.

The computing system 100 can include the multiphase upscaling module 106 to execute a first multiphase upscaling operation based on the absolute permeability of the physical rock sample and the absolute permeabilities of the synthetic rock samples. The multiphase upscaling module 106 may execute steady-state or unsteady-state upscaling. The multiphase upscaling module 106 can compute a relative permeability and capillary pressure for the physical rock sample and relative permeabilities and capillary pressures for the synthetic rock samples. The relative permeabilities and capillary pressures can be calculated using the absolute permeability and fractional flow information from two fluids flowing through a rock. For example, a combination of 50% water and 50% oil can be injected through the physical rock sample. In another example, a digital simulation can be used to determine the relative permeability and capillary pressure of the physical rock sample. The multiphase upscaling module 106 can execute similar operations for the synthetic rock samples to determine the relative permeabilities and capillary pressures of the synthetic rock samples. The relative permeabilities for the physical rock sample and the synthetic rock samples can be represented by curves showing relative permeability values at fractions of water saturation.

In some examples, the computing system 100 can include the synthetic rock selection module 108 to select a synthetic rock sample that best represents the physical rock sample. The synthetic rock selection module 108 can compare the relative permeability curve for the physical rock sample to the relative permeability curves for the synthetic rock samples to determine which synthetic rock sample varies the least from the physical rock sample. The synthetic rock selection module 108 can select the synthetic rock sample that varies the least from the physical rock sample as the synthetic rock sample that best represents the flow unit properties of the physical rock sample.

In some examples, the computing system 100 can execute the machine-learning module 110 to select the synthetic rock sample instead of executing the synthetic rock selection module 108. Training data can be used to train a neural network for selecting a synthetic rock sample. In an example, the training data can be historical data associated with relative permeability and capillary pressure curves for physical rock samples and synthetic rock samples. The machine-learning module 110 can use results from the multiphase upscaling module 106 to select the synthetic rock sample that best represents the contents of the physical rock sample. Machine learning can enable the computing system 100 to estimate flow unit properties needed for reservoir simulation and management from the pore to the core scale in areas outside of where physical data is present.

The computing system 100 can execute the additional multiphase upscaling module 112 on the physical rock sample and the synthetic rock samples to determine the second multiphase upscaling result 116. The additional multiphase upscaling module 112 can upscale the results from the scale of the plug or core sample to a larger scale, such as a lithofacies scale. Additionally or alternatively, the additional multiphase upscaling module 112 can upscale the results from the lithofacies scale to a reservoir scale. The result of upscaling to the reservoir scale can be represented by a second multiphase upscaling result 116.

In some examples, the computing system 100 can output the second multiphase upscaling result 116. A user may use the second multiphase upscaling result 116 in a reservoir simulation. The reservoir simulation can allow the user to create a plan for operating and managing the reservoir. For example, the reservoir simulation may indicate locations suitable for drilling wells or provide other properties relating to extraction operations.

Figure 2:
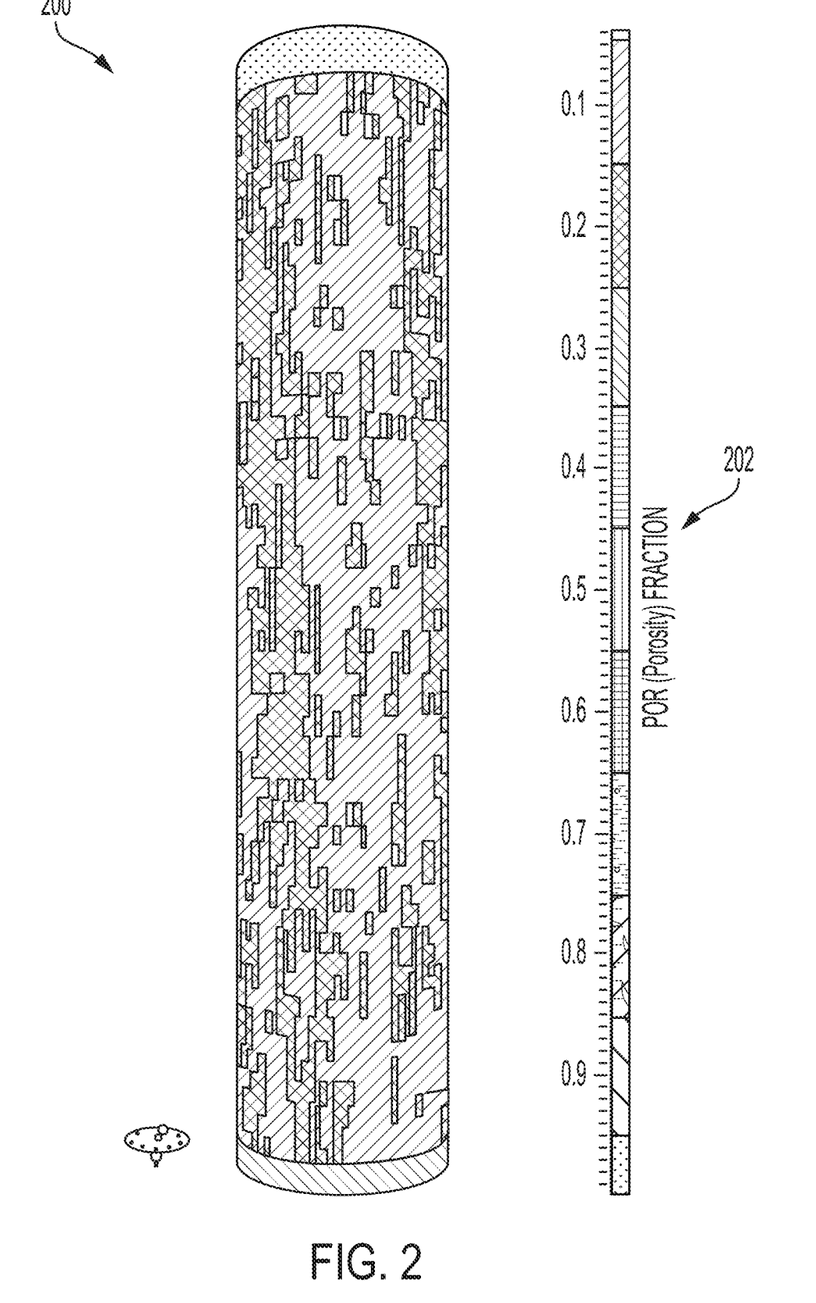
FIG. 2 is a schematic of a digital representation of a physical rock sample according to one example of the present disclosure.

FIG. 2 is a schematic of a digital representation of a physical rock sample 200 according to one example of the present disclosure. The physical rock sample of a plug or core sample containing multiple rock types can be converted to a digital model. For example, a photograph can be taken of the physical rock sample and, from the photograph, a porosity fraction 202 and other properties of the physical rock sample can be determined throughout the physical rock sample. A computing system can generate the digital representation of the physical rock sample 200 based on the properties of the physical rock sample determined from the photograph. The computing system can use the porosity fraction 202 and other measurements to determine a relative permeability and capillary pressure for the physical rock sample.

FIGS. 3A-3D are schematics of synthetic rock samples according to one example of the present disclosure. A computing system can generate synthetic rock samples based on the digital representation of a physical rock sample 200. The computing system can generate synthetic core samples that are geometrically similar to the physical rock sample and volumetrically different from each other. The computing system can determine relative permeabilities and capillary pressures for the synthetic rock samples, which will vary based on their volumetric and geometric properties. A porosity fraction 202 can be shown throughout the synthetic core samples.

Figure 3A:
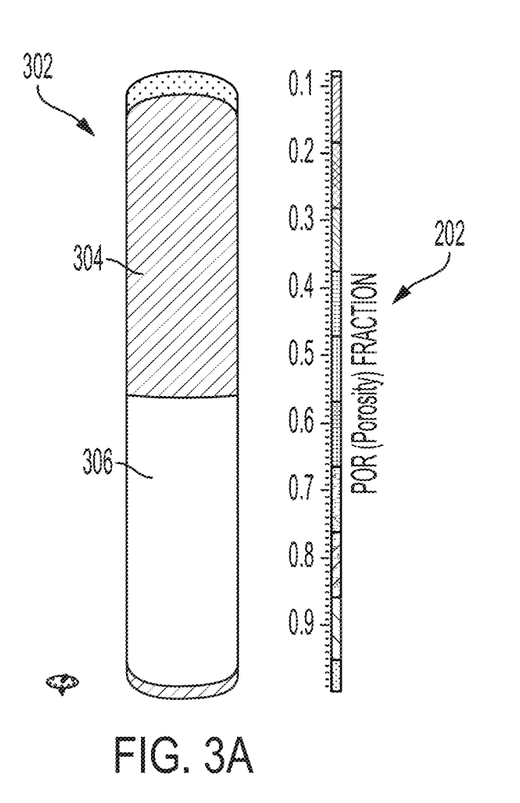
FIGS. 3A-3D are schematics of synthetic rock samples according to one example of the present disclosure.
Figure 3B:
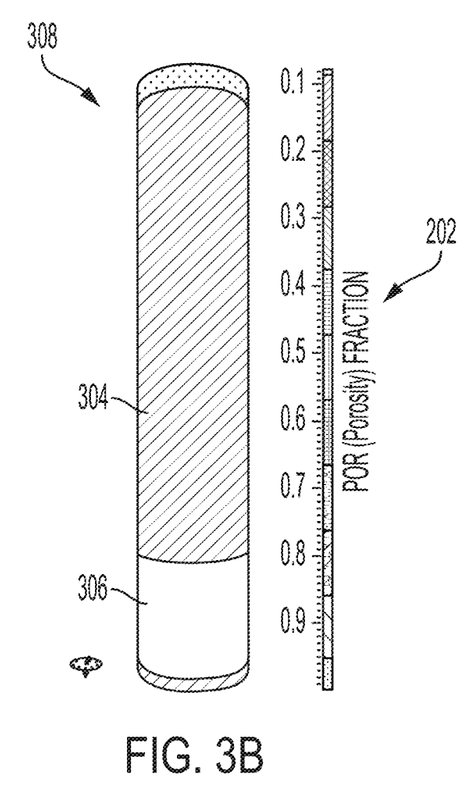

FIGS. 3A and 3B show a Synthetic Rock Sample A 302 and a Synthetic Rock Sample B 308 generated by the computing system based on the digital representation of the physical rock sample 200. For example, if the physical rock sample is made up of two types of rock that are arranged in series, the computing system can generate the Synthetic Rock Sample A 302 and the Synthetic Rock Sample B 308 that both contain Rock Type A 304 and Rock Type B 306 in series. The Synthetic Rock Sample A 302 can be composed of 50% Rock Type A 304 and 50% Rock Type B 306. Synthetic Rock Sample B 308 can be composed of 80% Rock Type A 304 and 20% Rock Type B 306.

Figure 3C:
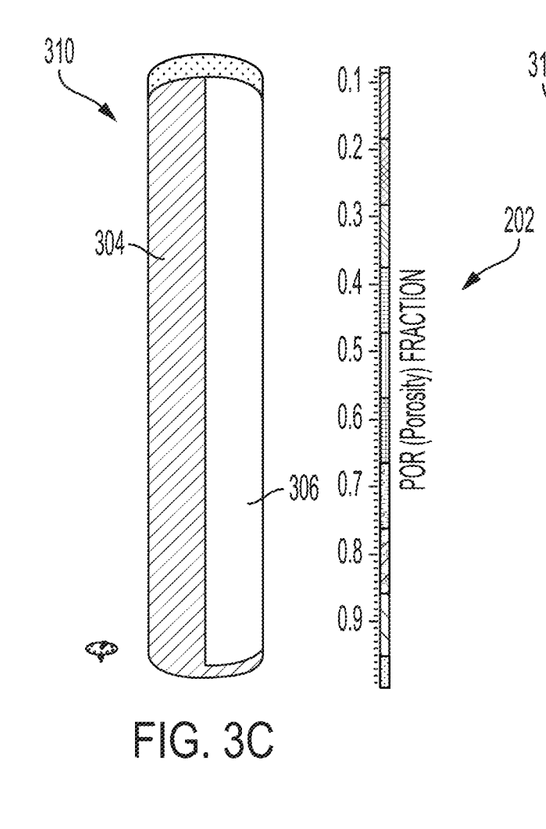
Figure 3D:
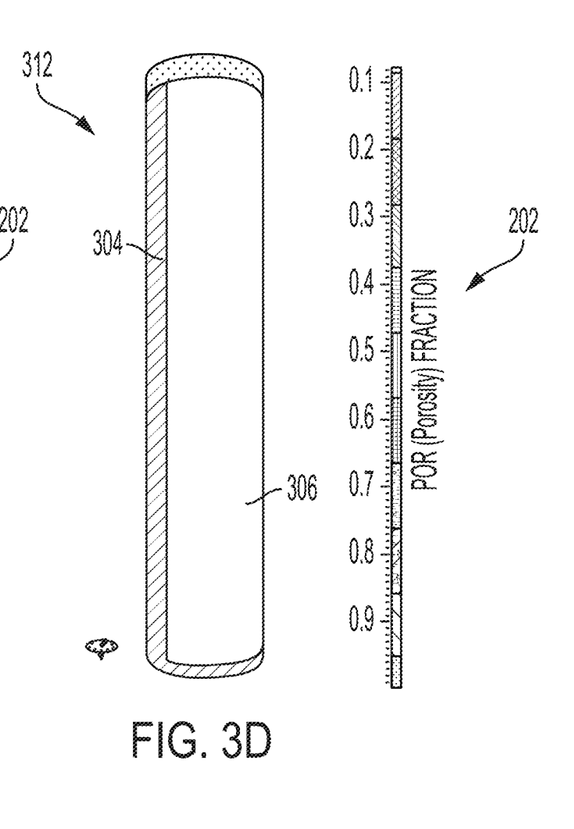

FIGS. 3C and 3D show a Synthetic Rock Sample C 310 and a Synthetic Rock Sample D 312 generated by the computing system based on the digital representation of the physical rock sample. For example, if the physical rock sample is made up of two types of rock that are arranged in parallel, the computing system can generate the Synthetic Rock Sample C 310 and the Synthetic Rock Sample D 312 that both contain Rock Type A 304 and Rock Type B 306 in parallel. The Synthetic Rock Sample C 310 can be composed of 50% Rock Type A 304 and 50% Rock Type B 306. Synthetic Rock Sample D 312 can be composed of 80% Rock Type A 304 and 20% Rock Type B 306.

Figure 4:
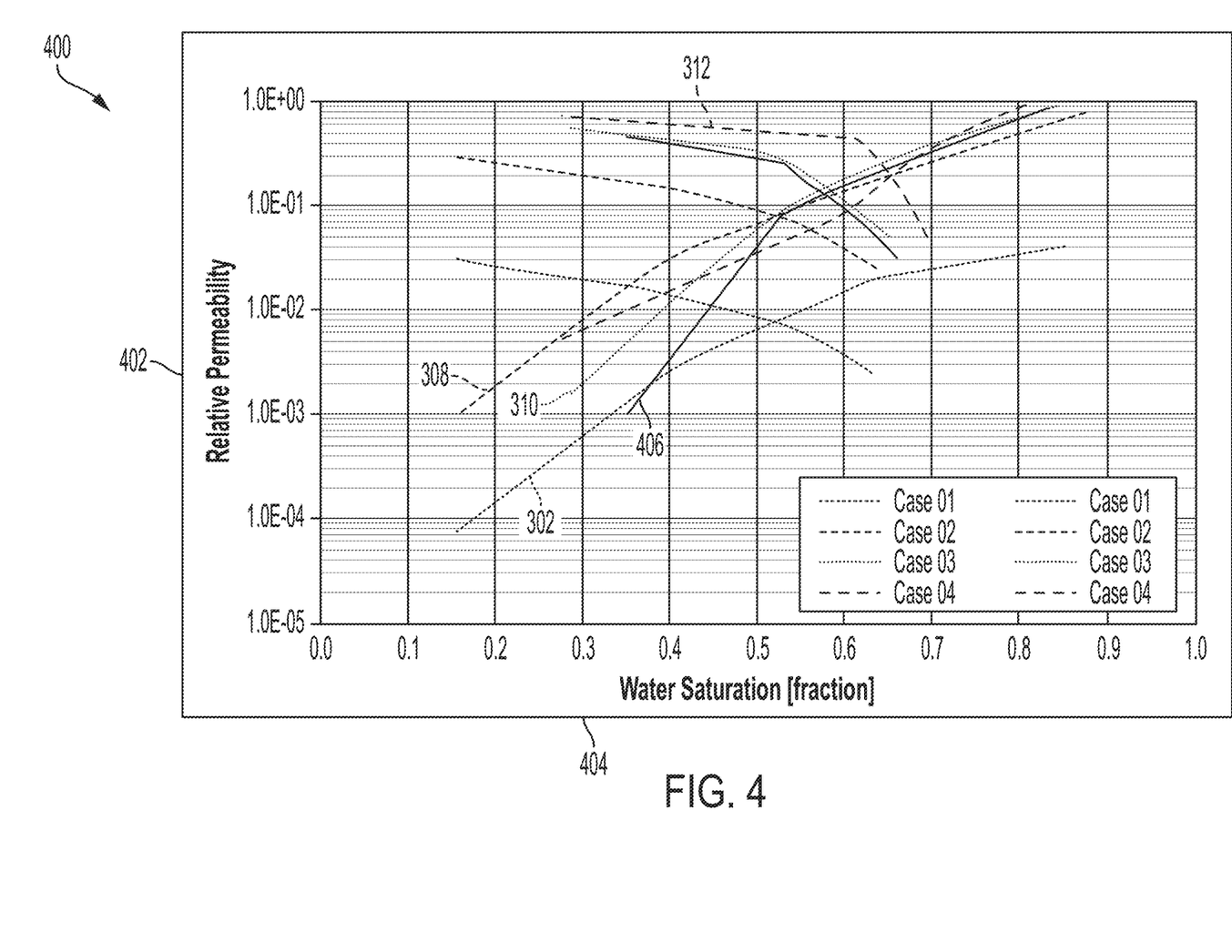
FIG. 4 is a graph of a comparison of the relative permeability and capillary pressures for a physical rock sample and synthetic rock samples according to one example of the present disclosure.

FIG. 4 is a graph 400 of relative permeabilities and capillary pressures for a physical rock sample 406 and synthetic rock samples according to one example of the present disclosure. A computing system can generate the graph 400 showing relative permeability 402 versus a water saturation fraction 404 for the physical rock sample 200 and a Synthetic Rock Sample A 302, a Synthetic Rock Sample B 308, a Synthetic Rock Sample C 310, and a Synthetic Rock Sample D 312. The graph 400 includes an increasing line and a decreasing line for each rock sample. The increasing line represents the relative permeability for the rock sample as water flows through the rock sample at an increasing fraction. The decreasing line represents the relative permeability for the rock sample as oil flows through the rock sample at a decreasing fraction. The lines intersect where the flow rate is the same for the water and oil flowing through the rock sample.

The computing system can compare the relative permeability of the physical rock sample 406 to the relative permeabilities of each of the synthetic rock samples. The computing system can determine which synthetic rock sample varies the least from the physical rock sample based on the comparison. For example, the computing system can determine physical rock sample 406 varies the least from the Synthetic Rock Sample C 310, so the relative permeability of the Synthetic Rock Sample C 310 best represents the flow unit properties of the physical rock sample 406.

Figure 5:
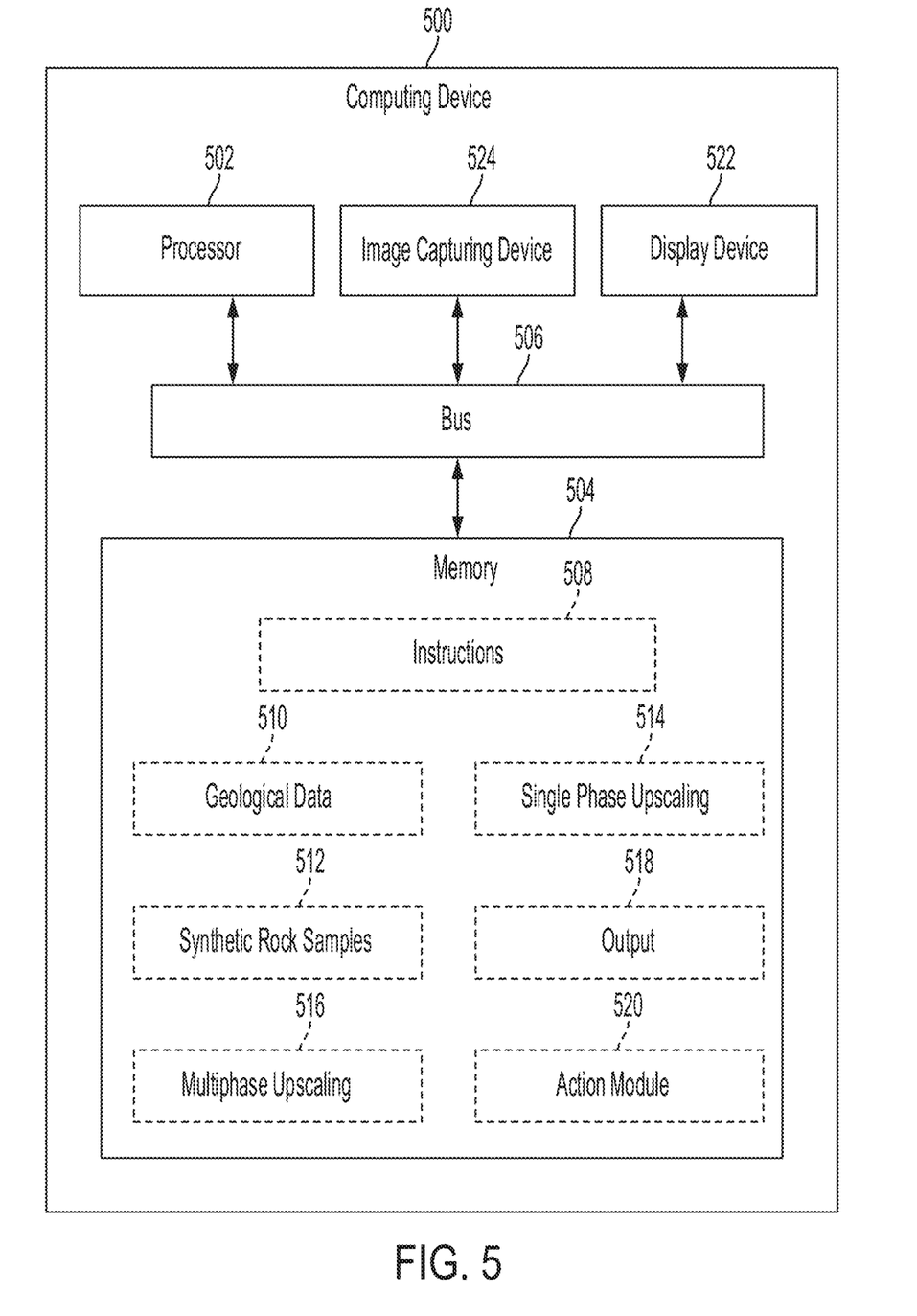
FIG. 5 is a block diagram of an example of a computing device for estimating of relative permeability and capillary pressures of a geological formation based on multiphase upscaling according to one example of the present disclosure.

FIG. 5 is a block diagram of an example of a computing device 500 for estimating relative permeability and capillary pressures of a geological formation based on multiphase upscaling according to one example of the present disclosure. The computing device 500 can include a processor 502, a bus 506, a memory 504, a display device 522, and an image capturing device 524. In some examples, the components shown in FIG. 5 can be integrated into a single structure. For example, the components can be within a single housing with a single processing device. In other examples, the components shown in FIG. 5 can be distributed (e.g., in separate housings) and in electrical communication with each other using various processors. It is also possible for the components to be distributed in a cloud computing system or grid computing system.

The processor 502 can execute one or more operations for estimating relative permeability and capillary pressures for a geological formation. The processor 502 can execute instructions stored in the memory 504 to perform the operations. The processor 502 can include one processing device or multiple processing devices. Non-limiting examples of the processor 502 include a field-programmable gate array ("FPGA"), an application-specific integrated circuit ("ASIC"), a processor, a microprocessor, etc.

The processor 502 is communicatively coupled to the memory 504 via the bus 506. The memory 504 may include any type of memory device that retains stored information when powered off. Non-limiting examples of the memory 504 include electrically erasable and programmable read-only memory ("EEPROM"), flash memory, or any other type of non-volatile memory. In some examples, at least some of the memory 504 can include a non-transitory medium from which the processor 502 can read instructions. A computer-readable medium can include electronic, optical, magnetic, or other storage devices capable of providing the processor 502 with computer-readable instructions or other program code. Non-limiting examples of a computer-readable medium include (but are not limited to) magnetic disk(s), memory chip(s), read-only memory (ROM), random-access memory ("RAM"), an ASIC, a configured processing device, optical storage, or any other medium from which a computer processing device can read instructions. The instructions can include processing device-specific instructions generated by a compiler or an interpreter from code written in any suitable computer-programming language, including, for example, C, C++, C#, etc.

In some examples, the computing device 500 includes a display device 522. The display device 522 can represent one or more components used to output data. Examples of the display device 522 can include a liquid-crystal display (LCD), a computer monitor, a touch-screen display, etc.

In some examples, the computing device 500 includes an image capturing device 524. The image capturing device 524 can be a camera or any other type of device capable of capturing an image of a physical rock sample.

The computing device 500 may include geological data 510 describing the physical rock sample. The computing device 500 can access the geological data 510 and generate synthetic rock samples 512 based on the number of rock types and the geometric arrangement of the rock types in the physical rock sample. The synthetic rock samples 512 can be geometrically similar to the physical rock sample and volumetrically different from each other. For example, if the computing device 500 determines the geological data 510 indicates that the physical rock sample has two rock types in parallel, the computing device 500 can generate synthetic rock samples 512 made of two rock types in parallel. Each of the synthetic rock samples 512 can have a different volumetric ratio of the two rock types.

The computing device 500 can execute single phase upscaling 514 on the physical rock sample and the synthetic rock samples 512 to determine absolute permeabilities of the physical rock and the synthetic rock samples 512. The computing device 500 can use the absolute permeabilities to execute multiphase upscaling 516 to determine relative permeabilities and capillary pressures for the physical rock sample and the synthetic rock samples 512. The computing device 500 can compare the relative permeability and capillary pressure of the physical rock sample to the relative permeabilities and capillary pressures of the synthetic rock samples 512 to determine which synthetic rock sample varies the least from the physical rock sample. The computing device 500 can select the synthetic rock sample that varies the least as the rock sample that best describes the properties of the physical rock sample. In some examples, computing device 500 can select the synthetic rock sample that best matches the physical rock sample using machine learning. Training data can be used to train a machine-learning model that can select the best synthetic rock sample.

The computing device 500 can perform the multiphase upscaling 516 multiple times to increase the scale from a plug or core sample level to a lithofacies or reservoir scale. The computing device 500 can generate an output 518 of the upscaled result. In some examples, the computing device 500 can include an action module 520 that can take the output 518 and apply it to some other process. For example, the computing device 500 can use the output 518 to control a well drilling operation or some other process relevant to the output 518. The action module 520 can apply the output 518 to develop a plan for drilling operations. The plan can include locations in the reservoir to drill wells to reduce the cost of production operations. Since the relative permeability and capillary pressure provide information about how fluids will flow in the rock, higher relative permeabilities in a location of the reservoir can indicate that fluids, such as oil, will flow more readily at that location. As a result, the plan for drilling can include a well at that location so the yield of extracted oil is greater.

Figure 6:
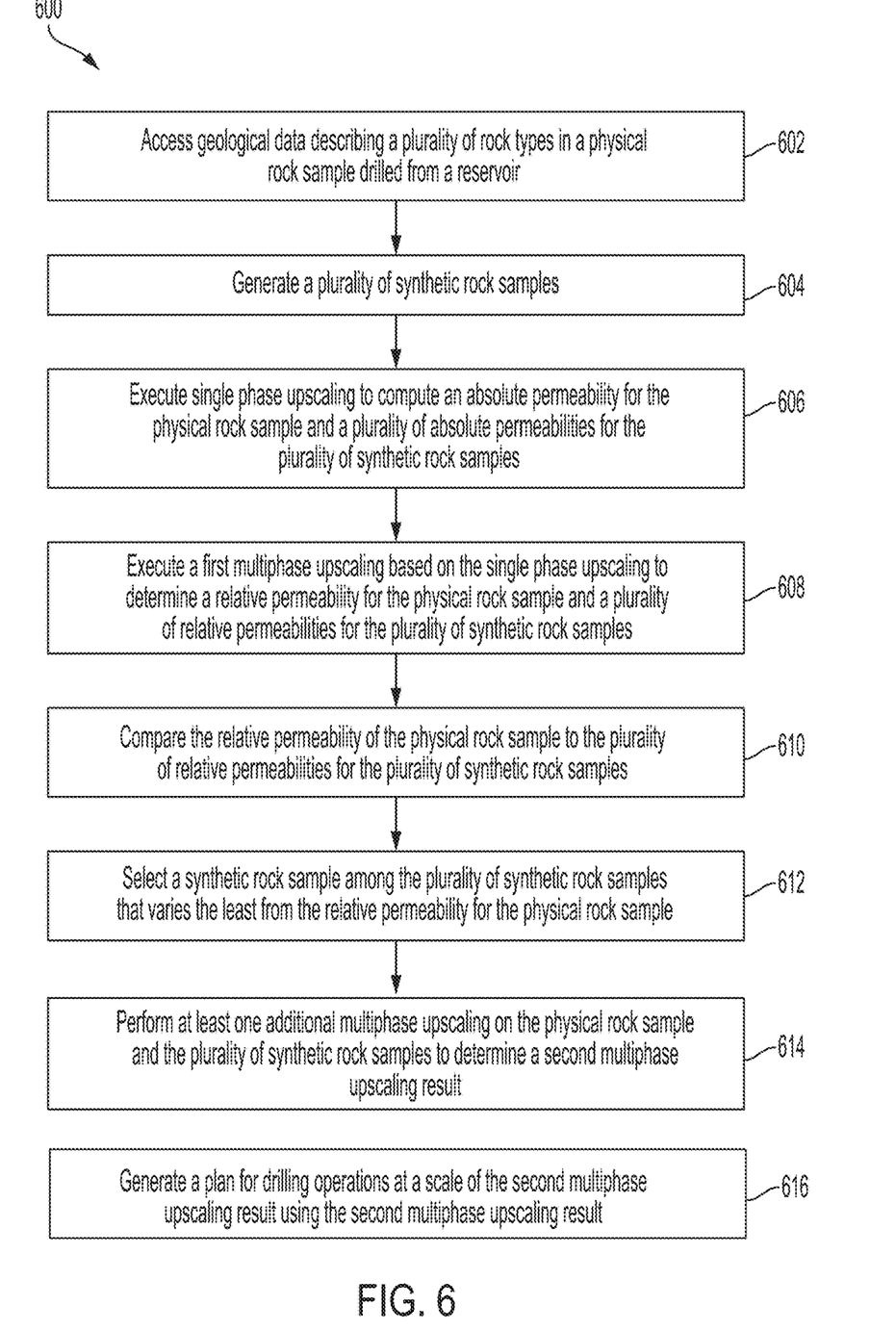
FIG. 6 is a flowchart of a process for estimating of relative permeability and capillary pressures of a geological formation based on multiphase upscaling according to one example of the present disclosure.

In some examples, the computing device 500 can implement the process 600 shown in FIG. 6 for effectuating some aspects of the present disclosure. Other examples can involve more operations, fewer operations, different operations, or a different order of the operations shown in FIG. 6. The operations of FIG. 6 are described below with reference to the components shown in FIG. 5.

In block 602, the processor 502 can access geological data 510 describing a plurality of rock types in a physical rock sample from a geological formation. The physical rock sample can be a plug or core sample. The geological data 510 can indicate the number of rock types present in the physical rock sample as well as geometric information for the arrangement of the plurality of rock types.

In block 604, the processor 502 can generate a plurality of synthetic rock samples 512. The plurality of synthetic rock samples 512 can be geometrically similar to the physical rock sample. The processor 502 can generate synthetic rock samples 512 that are volumetrically different from each other.

In block 606, the processor 502 can execute single phase upscaling 514 to compute an absolute permeability for the physical rock sample and a plurality of absolute permeabilities for the plurality of synthetic rock samples 512. The processor 502 can determine the absolute permeabilities by performing computer simulations for single-phase flow of a fluid through the physical rock sample and the plurality of synthetic rock samples 512.

In block 608, the processor 502 can execute a first multiphase upscaling 516 based on the single phase upscaling 514 to determine a relative permeability for the physical rock sample and a plurality of relative permeabilities for the plurality of synthetic rock samples 512. The processor 502 can perform additional operations using the absolute permeabilities to determine relative permeabilities for the physical rock sample and the plurality of synthetic rock samples 512.

In block 610, the processor 502 can compare the relative permeability of the physical rock sample to the plurality of relative permeabilities for the plurality of synthetic rock samples 512. The processor 502 can determine how much each of the synthetic rock samples 512 vary from the physical rock sample.

In block 612, the processor 502 can select a synthetic rock sample among the plurality of synthetic rock samples 512 that varies the least from the relative permeability for the physical rock sample. The synthetic rock sample that is selected can represent the flow unit properties of the physical rock sample. In some examples, the processor 502 can use machine learning to select the synthetic rock sample that varies the least from the relative permeability of the physical rock sample.

In block 614, the processor 502 can perform at least one additional multiphase upscaling 516 on the physical rock sample and the synthetic rock samples to determine a second multiphase upscaling result. The at least one additional multiphase upscaling 516 can be from a plug or core sample to a lithofacies scale or a reservoir scale.

In block 616, the processor 502 can generate a plan for drilling operations at a scale of the second multiphase upscaling result using the second multiphase upscaling result. For example, the second multiphase upscaling result can be at the reservoir scale and can be used in reservoir simulations so a user can create a plan for managing the reservoir. The plan can include locations in the reservoir to drill wells based on lowering the cost of production operations of the wells.

In some aspects, a system, a method, or a non-transitory computer-readable medium for estimating relative permeability and capillary pressures of a geological formation by multiphase upscaling of synthetic rock samples according to one or more of the following examples:

As used below, any reference to a series of examples is to be understood as a reference to each of those examples disjunctively (e.g., "Examples 1-4" is to be understood as "Examples 1, 2, 3, or 4").

Example 1 is a system comprising: a processing device; and a memory device that includes instructions executable by the processing device for causing the processing device to: access geological data describing a plurality of rock types in a physical rock sample drilled from a reservoir; generate a plurality of synthetic rock samples; execute single phase upscaling to compute an absolute permeability for the physical rock sample and a plurality of absolute permeabilities for the plurality of synthetic rock samples; execute a first multiphase upscaling based on the single phase upscaling to determine a relative permeability and capillary pressure for the physical rock sample and a plurality of relative permeabilities and capillary pressures for the plurality of synthetic rock samples; compare the relative permeability and capillary pressure of the physical rock sample to the plurality of relative permeabilities and capillary pressures of the plurality of synthetic rock samples; select a synthetic rock sample among the plurality of synthetic rock samples that varies the least from the relative permeability and capillary pressure for the physical rock sample; perform at least one additional multiphase upscaling on the physical rock sample and the plurality of synthetic rock samples to determine a second multiphase upscaling result; and generate a plan for drilling operations at a scale of the second multiphase upscaling result using the second multiphase upscaling result.

Example 2 is the system of example 1, wherein the memory device further includes instructions executable by the processing device for causing the processing device to select the synthetic rock sample using a machine learning algorithm trained with historical data of relative permeabilities and capillary pressures of physical rock samples and synthetic rock samples.

Example 3 is the system of examples 1-2, wherein the geological data includes a set of curves corresponding to relative permeability and capillary pressures for the plurality of rock types in the physical rock sample and each rock type in the plurality of rock types is assigned to a curve in the set of curves.

Example 4 is the system of examples 1-3, wherein the plurality of synthetic rock samples comprises synthetic rock samples that are volumetrically different from each other and geometrically similar to the physical rock sample.

Example 5 is the system of examples 1-4, wherein the physical rock sample is a plug or core sample from the reservoir.

6. The system of examples 1-5, wherein the first multiphase upscaling is from a plug or core scale to a lithofacies scale, and wherein the at least one additional multiphase upscaling is from the lithofacies scale to a reservoir scale.

Example 7 is the system of examples 1-6, wherein: the physical rock sample and the plurality of synthetic rock samples are plug or core samples; the plurality of synthetic rock samples comprises synthetic rock samples that are volumetrically different from each other and geometrically similar to the physical rock sample; the first multiphase upscaling and the at least one additional multiphase upscaling are based on a fluid combination of oil and water; the first multiphase upscaling is from a plug or core scale to a lithofacies scale; the at least one additional multiphase upscaling is from a lithofacies scale to a reservoir scale; and the memory device further includes instructions executable by the processing device for causing the processing device to output the second multiphase upscaling result to a user to allow the user to create a plan for extraction operations for the reservoir.

Example 8 is the system of examples 1-7, wherein the memory device further includes instructions executable by the processing device for causing the processing device to: control an image capturing device to capture an image of the physical rock sample; and generate a digital representation of the physical rock sample from the image of the physical rock sample, the digital representation including geological data of the physical rock sample.

Example 9 is a method, comprising: accessing geological data describing a plurality of rock types in a physical rock sample drilled from a reservoir; generating a plurality of synthetic rock samples; executing single phase upscaling to compute an absolute permeability for the physical rock sample and a plurality of absolute permeabilities for the plurality of synthetic rock samples; executing a first multiphase upscaling based on the single phase upscaling to determine a relative permeability and capillary pressure for the physical rock sample and a plurality of relative permeabilities and capillary pressures for the plurality of synthetic rock samples; comparing the relative permeability and capillary pressure of the physical rock sample to the plurality of relative permeabilities and capillary pressures for the plurality of synthetic rock samples; selecting a synthetic rock sample among the plurality of synthetic rock samples that varies the least from the relative permeability and capillary pressure for the physical rock sample; performing at least one additional multiphase upscaling on the physical rock sample and the plurality of synthetic rock samples to determine a second multiphase upscaling result; and generate a plan for drilling operations at a scale of the second multiphase upscaling result using the second multiphase upscaling result.

Example 10 is the method of example 9, wherein selecting the rock sample comprises using a machine learning algorithm.

Example 11 is the method of examples 9-10, wherein the geological data includes a set of curves corresponding to relative permeability and capillary pressures for the plurality of rock types in the physical rock sample and each rock type in the plurality of rock types is assigned to a curve in the set of curves.

Example 12 is the method of examples 9-11, wherein the plurality of synthetic rock samples comprises synthetic rock samples that are volumetrically different from each other and geometrically similar to the physical rock sample.

Example 13 is the method of examples 9-12, wherein the physical rock sample is a plug or core sample from the reservoir.

Example 14 is the method of examples 9-13, wherein the at least one additional multiphase upscaling is from a lithofacies scale to a reservoir scale.

Example 15 is the method of examples 9-14, further comprising outputting the second multiphase upscaling result to a user to allow the user to create a plan for extraction operations for the reservoir.

Example 16 is a non-transitory computer-readable medium comprising instructions that are executable by a processing device for causing the processing device to: access geological data describing a plurality of rock types in a physical rock sample drilled from a reservoir; generate a plurality of synthetic rock samples; execute single phase upscaling to compute an absolute permeability for the physical rock sample and a plurality of absolute permeabilities for the plurality of synthetic rock samples; execute a first multiphase upscaling based on the single phase upscaling to determine a relative permeability and capillary pressure for the physical rock sample and a plurality of relative permeabilities and capillary pressures for the plurality of synthetic rock samples; compare the relative permeability and capillary pressure of the physical rock sample to the plurality of relative permeabilities and capillary pressures for the plurality of synthetic rock samples; select a synthetic rock sample among the plurality of synthetic rock samples that varies the least from the relative permeability and capillary pressure for the physical rock sample; perform at least one additional multiphase upscaling on the physical rock sample and the plurality of synthetic rock samples to determine a second multiphase upscaling result; and generate a plan for drilling operations at a scale of the second multiphase upscaling result using the second multiphase upscaling result.

Example 17 is the non-transitory computer-readable medium of example 16, further comprising instructions that are executable by the processing device for causing the processing device to select the rock sample using a machine learning algorithm.

Example 18 is the non-transitory computer-readable medium of examples 16-17, wherein the geological data includes a set of curves corresponding to relative permeability and capillary pressures for the plurality of rock types in the physical rock sample and each rock type in the plurality of rock types is assigned to a curve in the set of curves.

Example 19 is the non-transitory computer-readable medium of examples 16-18, wherein the plurality of synthetic rock samples comprises synthetic rock samples that are volumetrically different from each other and geometrically similar to the physical rock sample.

Example 20 is the non-transitory computer-readable medium of examples 19, wherein the at least one additional multiphase upscaling is from a lithofacies scale to a reservoir scale.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A system comprising:
   a processing device; and
   a memory device that includes instructions executable by the processing device for causing the processing device to:
   control an image capturing device to capture an image of a physical rock sample drilled from a reservoir;
   generate a digital representation of the physical rock sample from the image of the physical rock sample, the digital representation including geological data of the physical rock sample;
   access the geological data describing a plurality of rock types in the physical rock sample;
   generate a plurality of synthetic rock samples;
   execute single phase upscaling to compute an absolute permeability for the physical rock sample and a plurality of absolute permeabilities for the plurality of synthetic rock samples;
   execute a first multiphase upscaling based on the single phase upscaling to determine a relative permeability and capillary pressure for the physical rock sample and a plurality of relative permeabilities and capillary pressures for the plurality of synthetic rock samples;
   compare the relative permeability and capillary pressure of the physical rock sample to the plurality of relative permeabilities and capillary pressures of the plurality of synthetic rock samples;
   select a synthetic rock sample among the plurality of synthetic rock samples that varies the least from the relative permeability and capillary pressure for the physical rock sample;
   perform at least one additional multiphase upscaling on the physical rock sample and the plurality of synthetic rock samples to determine a second multiphase upscaling result; and
   generate a plan for drilling operations at a scale of the second multiphase upscaling result using the second multiphase upscaling result.

2. The system of claim 1, wherein the memory device further includes instructions executable by the processing device for causing the processing device to select the synthetic rock sample using a machine learning algorithm trained with historical data of relative permeabilities and capillary pressures of physical rock samples and synthetic rock samples.

3. The system of claim 1, wherein the geological data includes a set of curves corresponding to relative permeability and capillary pressures for the plurality of rock types in the physical rock sample and each rock type in the plurality of rock types is assigned to a curve in the set of curves.

4. The system of claim 1, wherein the plurality of synthetic rock samples comprises synthetic rock samples that are volumetrically different from each other and geometrically similar to the physical rock sample.

5. The system of claim 1, wherein the physical rock sample is a plug or core sample from the reservoir.

6. The system of claim 1, wherein the first multiphase upscaling is from a plug or core scale to a lithofacies scale, and wherein the at least one additional multiphase upscaling is from the lithofacies scale to a reservoir scale.

7. The system of claim 1, wherein:
   the physical rock sample and the plurality of synthetic rock samples are plug or core samples;
   the plurality of synthetic rock samples comprises synthetic rock samples that are volumetrically different from each other and geometrically similar to the physical rock sample;
   the first multiphase upscaling and the at least one additional multiphase upscaling are based on a fluid combination of oil and water;
   the first multiphase upscaling is from a plug or core scale to a lithofacies scale;
   the at least one additional multiphase upscaling is from a lithofacies scale to a reservoir scale; and
   the memory device further includes instructions executable by the processing device for causing the processing device to output the second multiphase upscaling result to a user to allow the user to create a plan for extraction operations for the reservoir.

8. A method, comprising:
   controlling an image capturing device to capture an image of a physical rock sample drilled from a reservoir;
   generating a digital representation of the physical rock sample from the image of the physical rock sample, the digital representation including geological data of the physical rock sample;
   accessing the geological data describing a plurality of rock types in the physical rock sample;
   generating a plurality of synthetic rock samples;
   executing single phase upscaling to compute an absolute permeability for the physical rock sample and a plurality of absolute permeabilities for the plurality of synthetic rock samples;
   executing a first multiphase upscaling based on the single phase upscaling to determine a relative permeability and capillary pressure for the physical rock sample and a plurality of relative permeabilities and capillary pressures for the plurality of synthetic rock samples;

comparing the relative permeability and capillary pressure of the physical rock sample to the plurality of relative permeabilities and capillary pressures for the plurality of synthetic rock samples;

selecting a synthetic rock sample among the plurality of synthetic rock samples that varies the least from the relative permeability and capillary pressure for the physical rock sample;

performing at least one additional multiphase upscaling on the physical rock sample and the plurality of synthetic rock samples to determine a second multiphase upscaling result; and generate a plan for drilling operations at a scale of the second multiphase upscaling result using the second multiphase upscaling result.

9. The method of claim 8, wherein selecting the rock sample comprises using a machine learning algorithm.

10. The method of claim 8, wherein the geological data includes a set of curves corresponding to relative permeability and capillary pressures for the plurality of rock types in the physical rock sample and each rock type in the plurality of rock types is assigned to a curve in the set of curves.

11. The method of claim 8, wherein the plurality of synthetic rock samples comprises synthetic rock samples that are volumetrically different from each other and geometrically similar to the physical rock sample.

12. The method of claim 8, wherein the physical rock sample is a plug or core sample from the reservoir.

13. The method of claim 8, wherein the at least one additional multiphase upscaling is from a lithofacies scale to a reservoir scale.

14. The method of claim 8, further comprising outputting the second multiphase upscaling result to a user to allow the user to create a plan for extraction operations for the reservoir.

15. A non-transitory computer-readable medium comprising instructions that are executable by a processing device for causing the processing device to:

control an image capturing device to capture an image of a physical rock sample drilled from a reservoir;

generate a digital representation of the physical rock sample from the image of the physical rock sample, the digital representation including geological data of the physical rock sample;

access the geological data describing a plurality of rock types in the physical rock sample;

generate a plurality of synthetic rock samples;

execute single phase upscaling to compute an absolute permeability for the physical rock sample and a plurality of absolute permeabilities for the plurality of synthetic rock samples;

execute a first multiphase upscaling based on the single phase upscaling to determine a relative permeability and capillary pressure for the physical rock sample and a plurality of relative permeabilities and capillary pressures for the plurality of synthetic rock samples;

compare the relative permeability and capillary pressure of the physical rock sample to the plurality of relative permeabilities and capillary pressures for the plurality of synthetic rock samples;

select a synthetic rock sample among the plurality of synthetic rock samples that varies the least from the relative permeability and capillary pressure for the physical rock sample;

perform at least one additional multiphase upscaling on the physical rock sample and the plurality of synthetic rock samples to determine a second multiphase upscaling result; and generate a plan for drilling operations at a scale of the second multiphase upscaling result using the second multiphase upscaling result.

16. The non-transitory computer-readable medium of claim 15, further comprising instructions that are executable by the processing device for causing the processing device to select the rock sample using a machine learning algorithm.

17. The non-transitory computer-readable medium of claim 15, wherein the geological data includes a set of curves corresponding to relative permeability and capillary pressures for the plurality of rock types in the physical rock sample and each rock type in the plurality of rock types is assigned to a curve in the set of curves.

18. The non-transitory computer-readable medium of claim 15, wherein the plurality of synthetic rock samples comprises synthetic rock samples that are volumetrically different from each other and geometrically similar to the physical rock sample.

19. The non-transitory computer-readable medium of claim 15, wherein the at least one additional multiphase upscaling is from a lithofacies scale to a reservoir scale.

* * * * *